US010042023B2

(12) United States Patent
Warr

(10) Patent No.: US 10,042,023 B2
(45) Date of Patent: Aug. 7, 2018

(54) METHOD FOR MEASURING THE EMOTIONAL RESPONSE TO OLFACTIVE STIMULI

(75) Inventor: Jonathan Frank Warr, Paris (FR)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 272 days.

(21) Appl. No.: 13/403,612

(22) Filed: Feb. 23, 2012

(65) Prior Publication Data

US 2012/0220857 A1 Aug. 30, 2012

(30) Foreign Application Priority Data

Feb. 24, 2011 (EP) ..................... 11305196

(51) Int. Cl.
*G01R 33/48* (2006.01)
*A61B 5/055* (2006.01)

(52) U.S. Cl.
CPC .......... *G01R 33/4806* (2013.01); *A61B 5/055* (2013.01)

(58) Field of Classification Search
CPC ............................. G01R 33/4806; A61B 5/055
USPC ....................................................... 600/411
See application file for complete search history.

(56) References Cited

U.S. PATENT DOCUMENTS

| | | | | |
|---|---|---|---|---|
| 6,325,475 | B1 * | 12/2001 | Hayes | A61B 5/00 128/203.11 |
| 7,565,193 | B2 * | 7/2009 | Laken | A61B 5/0476 600/300 |
| 8,255,267 | B2 * | 8/2012 | Breiter | G06Q 10/00 705/14.42 |
| 2001/0053878 | A1 * | 12/2001 | Ferris | A61B 5/0555 600/415 |
| 2006/0036153 | A1 | 2/2006 | Laken | |
| 2007/0148293 | A1 * | 6/2007 | Lindsay | B65D 5/42 426/112 |
| 2008/0040082 | A1 * | 2/2008 | Stanton | G06Q 10/04 703/2 |
| 2008/0065468 | A1 * | 3/2008 | Berg | G06Q 30/0203 705/7.32 |
| 2008/0095731 | A1 | 4/2008 | Mitra | |
| 2009/0318773 | A1 * | 12/2009 | Jung | G06F 19/363 600/300 |
| 2010/0174586 | A1 | 7/2010 | Berg, Jr. et al. | |
| 2011/0028859 | A1 * | 2/2011 | Chian | A61B 5/04001 600/554 |

FOREIGN PATENT DOCUMENTS

CN 101512574 A 8/2009

OTHER PUBLICATIONS

V Bragulat, M Dzemidzic, C Bruno, CA Cox, T Talavage, RV Considine and DA Kareken, "Food-Related Odor Probes of Brain Reward Circuits During Hunger: A Pilot fMRI Study", 2010, Obesity, vol. 18, pp. 1566-1571.*

HC Breiter and BR Rosen, "Functional Magnetic Resonance Imaging of Brain Reward Circuitry in the Human", Jun. 1999, Annals of the New York Academy of Sciences, vol. 877, Advancing from the Ventral Striatum to the Extended Amygdala: Implications for Neuropsychiatry and Drug Abuse, pp. 523-547.*
R.S. Herz, J Eliassen, S Beland, T Souza, 2004, "Neuroimaging evidence for the emotional potency of odor-evoked memory", Neuropsychologica, vol. 42, pp. 371-378.*
M. Rosen, "Chapter 3: Brain Imaging", Feb. 28, 2007, The Brain and Love, Chelsea House Publishers, pp. 43-45.*
https://github.com/max-talanov/1 /blob/master/ affective%20computing/neurotransmission.md.*
DM Yousem, JA Maldjian, T Hummel, DC Alsop, RJ Geckle, MA Kraut, RL Doty, "The Effect of Age on Odor-Stimulated Functional MR Imaging", 1999, Am J Neuroradiol, vol. 20, pp. 600-608.*
V Smejkal, R Druga and J Tintera, "Olfactory activity in the human brain identified by fMRI", 2003, Bratisl Lek Listy, vol. 104, No. 6, pp. 184-188.*
https://github.eom/maxtalanov/1/blob/master/ affective%20eomputing/neurotransmission.md.*
F Grabenhorst, ET Rolls, Christian Margot, MAAP da Silva, and MI Velazco, "How Pleasant and Unpleasant Stimuli Combine in Different Brain Regions: Odor Mixtures", The Journal of Neuroscience, 2007, 27(49), pp. 13532-13540.*
European Search Report, issued by the European Patent Office in corresponding International Application No. 11305196.5 dated Jul. 19, 2011.
Murata, Yoriko et al., "Effects of olfactory stimulation with isovaleric acid on brain activation in informed and naive conditions: A functional MRI study," Auris Nasus Larynx, Tokyo, vol. 24, No. 4, Oct. 23, 2007, pp. 465-469.
Westermann, B. et al., "Functional imaging of the cerebral olfactory system in patients with Parkinson's disease," Journal of Neurology Neurosurgery & Psychiatry, BMJ Publishing Group, GB, vol. 79, No. 1, 2008, pp. 19-24.
Smejkal, V. et al., "Olfactory activity in the human brain identified by fMRI," Bratisl Lek Listy, SAP-Slovak Academic Press, Bratislava, SK, vol. 104, No. 6, 2003, pp. 184-188.
Gottfried, Jay A. et al., "Appetitive and Aversive Olfactory Learning in Humans Studied Using Event-Related Function Magnetic Resonance Imaging," The Journal of Neuroscience, vol. 22, No. 24, Dec. 15, 2002, pp. 10829-10837.
Kobal, Gerd et al., "Olfactory functional imaging and physiology," International Journal of Psychophysiology, vol. 36, No. 2, May 1, 2000, pp. 157-163.
Popp, Roland et al., "Olfactometry in fMRI studies: odor presentation using nasal continuous positive airway pressure," Acta Neurobiologiae Experimentalis, vol. 54, No. 2, 2004, pp. 171-176.
Kitabgi, Patrick, "Neurotensin Modulates Dopamine Neurotransmission at Several Levels Along Brain Dopaminergic Pathways," Neurochemistry International, vol. 14, No. 2, 1989, pp. 111-119.

(Continued)

*Primary Examiner* — Amanda Lauritzen Moher
*Assistant Examiner* — Lisa Kinnard
(74) *Attorney, Agent, or Firm* — Sughrue Mion, PLLC

(57) ABSTRACT

The invention relates to a method of identifying a fragrance sample using functional Magnetic Resonance Imaging to assess the ability of said fragrance sample to elicit a reward through the dopaminergic pathway; a fragrance sample identified by the method, and a method for preparing an accord or a fully formulated fragrance.

12 Claims, No Drawings

(56) References Cited

OTHER PUBLICATIONS

Borromeo, Susana et al., "Objective Assessment of Olfactory Function Using Functional Magnetic Resonance Imaging (fMRI)," IEEE Transactions on Instrumentation and Measurement, vol. 59, No. 10, Oct. 2010, pp. 2602-2608.

Arias-Carrion, Oscar, et al., "Dopaminergic reward system: a short integrative review," International Archives of Medicine, vol. 3, No. 24, Oct. 6, 2010, pp. 1-6.

Zatorre, Robert J., et al, "Neural mechanisms involved in odor pleasantness and intensity judgments," NeuroReport, vol. 11, No. 12, Aug. 21, 2000, pp. 2711-2716.

Communication, Issued by the State Intellectual Property Office of P.R. China, dated Nov. 3, 2014, in counterpart Chinese Application No. 201210042731.3.

Office Action issued by the State Intellectual Property Office of P.R. China dated Jul. 7, 2015, in counterpart Chinese Application No. 201210042731.3.

Office Action, dated Jan. 25, 2016, issued by the State Intellectual Property Office of P.R. China in counterpart Chinese Application No. 201210042731.3. Y.

* cited by examiner

METHOD FOR MEASURING THE EMOTIONAL RESPONSE TO OLFACTIVE STIMULI

CROSS-REFERENCE TO RELATED APPLICATIONS

This application claims priority from European Patent Application No. 11 305 196.5 filed on Feb. 24, 2011, the entire subject matter of which is incorporated herein by reference.

BACKGROUND OF THE INVENTION

Technical Field of the Invention

The invention relates to the use of a quantitative functional MRI (fMRI), mapping technique to discern human responses to olfactive stimuli in particular stimuli by fragrance ingredients, accords or fully formulated fragrances which induce a reward effect.

Background Art

Traditional consumer research techniques have only limited success in predicting whether a product will be a commercial success or not. It is desirable to have a technique of measuring brain response to stimuli without the time and reflection required in formulating and expressing ideas verbally, in response to questions. Magnetic resonance imaging techniques offer a way of investigating how a consumer responds to a stimulus in a non verbal way while the brain interprets the stimulus; it allows visualization of both primary response (e.g. in the piriform cortex, PC) and further processing of the sensory signals (e.g. in the orbitofrontal cortex, OFC). The consumer has to use, or experience the product in order to react to it and in the context of measuring brain response by MRI this may be difficult for many products. However it is possible to introduce olfactive stimuli to subjects in an accurate and precise way, whilst measuring brain response, using a specific form of olfactometer.

An olfactometer is a device designed to provide a number of olfactive stimuli to subjects in a controlled and reproducible way. The requirements of the MRI scanning technique impose restrictions on the design of olfactometers suitable for use in conjunction with MRI scanners. One major restriction is the elimination of magnetic materials from within the vicinity of the scanner. Due to the availability of olfactometers which can be used in conjunction with MRI scanners the interest in measuring brain response by MRI to olfactive stimuli has increased significantly in the past few years. Most of the interest in MRI measurement with olfaction has centered on hedonic responses to stimuli (see for example Zatorre R. L. Jones-Gottman M, Rouby C, *Neural mechanisms involved in odor pleasantness and intensity judgements* Neuroreport 11 2711-2716 (2000) or Kobal G, Kettenmann B, *Int. J. Psychophysiology* 36 (2) 157-163 2000).

A widely held view on emotional response is that we have 6 basic emotions (Ekman et al, *J of Personality and Social Psychology* 1987 v53, p 712):

Anger
Disgust
Fear
Happiness
Sadness
Surprise.

These emotions are related to reward, but reward is an effect of activating these emotions; in fact, an outcome of activation of all of these emotions may be reward (if you overcome fear than you are brave and will be rewarded; next time maybe you will be seeking fear to experience this reward etc.).

The dopaminergic pathway is sometimes called the reward pathway, and is generally associated with functions such as:

motivation and emotional response
reward and desire
pleasure, euphoria
addiction, compulsion.

Rewards are generally experienced as "making things better" and are thus liked, desired, and pursued. Reward may be expressed using words or expressions that communicate an intense feeling of well-being.

The areas of the brain involved in the dopaminergic pathway are well understood, and general descriptions can be found in a standard text such as *The Brain Atlas*, T. A. Woolset et al (Wiley 2008, ISBN 978-0-470-08476-2), with more specific details in review articles such as "*Dopaminergic reward system: a short integrative review*" by O. Arrias-Carrion et al, *International Archives of Medicine* 2010, 3:24, and in Everitt et al, *Brain Res Brain Res Review* 36, p 129-138 (2001). The pathway involves the Ventral Tegmental Area (located in the dopaminergic Midbrain), Nucleus Accumbens, Striatum (Caudate Nucleus and Putamen), Amygdala, Hippocampus and Prefrontal Cortex (Superior, Middle, Inferior frontal gyrus) and Anterior Cingulate gyrus.

In a review of fMRI studies using diverse stimuli, Sharpley and Bitsika (*Behav Brain Res* 2010 Jul. 13) note that the Ventral Tegmental Area (VTA) was activated by both maternal and romantic love, and commented that in almost all studies of love, humour and other forms of pleasure, the areas activated are also those associated with reward processes. Sharpley et al. also noted that activation of the VTA and Nucleus Accumbens was also associated with Joy/Happiness/Laughter, and this can be understood in the context that they are often the rewarding outcomes of an emotional experience.

SUMMARY OF THE INVENTION

Normally stimulation of the dopamine pathway is achieved by "strong" stimuli; photographs of loved ones, monetary reward etc. There is no evidence to date that a pleasant odour can activate the dopamine pathway. Surprisingly the present inventors have found that this pathway can be activated by the smelling of a fragrance sample (as defined below). Even more surprisingly, the present inventors have found that some, but not all fragrance samples, elicit a reward through the dopaminergic pathway, and have designed a method using fMRI imaging to screen for materials of interest. The same method can be used directly to evaluate any olfactive stimulus for its ability to stimulate the reward pathway.

In one aspect, the present invention provides a method of identifying a fragrance sample which elicits a reward through the dopaminergic pathway, wherein the method comprises:

a) submitting a group of subjects to an fMRI test during which each subject smells a control odour and a test fragrance sample;
b) capturing fMRI brain scans of each subject smelling the control odour and the test fragrance sample so as to detect the brain activity of each subject;

c) averaging the brain activity of all subjects when smelling the control odour and the test fragrance sample, respectively; and d) contrasting the averaged brain activity of the subjects when smelling the test fragrance sample with the averaged brain activity of the subjects when smelling the control odour.

In a further aspect, the present invention provides a fragrance sample identified by the above-mentioned method.

In yet a further aspect, the present invention provides a method of preparing a fragrance, for example a fully formulated fragrance, which comprises identifying a fragrance sample which elicits a reward through the dopaminergic pathway and formulating said sample into a fragrance.

In yet a further aspect, the present invention relates to the use of a fragrance sample which elicits a reward through the dopaminergic pathway in a consumer product.

That is, the invention encompasses the following embodiments.

(1) A method of identifying a fragrance sample which elicits a reward through a dopaminergic pathway, wherein the method comprises:

a) submitting a group of subjects to a first protocol comprising:
  having each subject of said group smell a control odour;
  capturing functional Magnetic Resonance Imaging (fMRI) brain scans of each subject smelling the control odour so as to detect a brain activity of each subject;

b) submitting the same group of subjects to a second protocol comprising:
  having each subject of said group smell a fragrance sample to be tested;
  capturing fMRI brain scans of each subject smelling the fragrance sample to be tested so as to detect a brain activity of each subject;

c) averaging the brain activity of all subjects as obtained in the first protocol and in the second protocol; and d) contrasting the resulting averaged brain activity obtained in the second protocol with the resulting averaged brain activity obtained in the first protocol whereby a number of adjacent activated voxels is determined;

wherein if a cluster of adjacent activated voxels has a volume equal to or greater than a threshold value, or if a cluster has a number of adjacent activated voxels equal to or greater than a threshold value in at least three of the following brain areas: the Midbrain (VTA), Prefrontal Cortex, Striatum and Amygdala-Hippocampus complex, then the tested fragrance sample elicits a reward through the dopaminergic pathway.

(2) The method according to (1), wherein the control odour is air or an odourless perfumery solvent diluted in air.

(3) The method according to (1) or (2), wherein the group of subjects comprises at least 5 subjects.

(4) The method according to (1) or (2), wherein the group of subjects comprises at least 10 subjects.

(5) The method according to any one of (1) to (4), wherein the threshold value of the volume that the cluster of adjacent activated voxels has is about 303 $mm^3$.

(6) The method according to any one of (1) to (4), wherein the threshold value of the number of adjacent activated voxels is nine.

(7) A fragrance sample identified by the method according to any one of (1) to (6).

(8) A method for preparing an accord or a fully formulated fragrance which comprises:

a) screening at least one fragrance sample for its (their) ability to elicit a reward through the dopaminergic pathway;

b) if the fragrance sample(s) is (are) identified to elicit a reward through the dopaminergic pathway, formulating said fragrance sample(s) into an accord or a fully formulated fragrance;

wherein step a) is carried out by the method defined in any one of (1) to (6).

(9) The method according to (8), wherein the accord or the fully formulated fragrance comprises vanillin.

(10) Use of a fragrance sample identified to elicit a reward through the dopaminergic pathway in a household product, a laundry product, a personal care product or a cosmetic product.

(11) A method of imparting a reward to a product, the method comprising formulating the fragrance sample identified to elicit a reward through the dopaminergic pathway by the method according to any one of (1) to (6) into a product, wherein the product is selected from the group consisting of a household product, a laundry product, a personal care product and a cosmetic product.

DETAILED DESCRIPTION OF THE INVENTION

All documents cited herein are incorporated by reference.

Definition

As used herein, the term "brain activity" means physiological and biochemical activity within the human brain, or a region of the brain, associated with mental activity, including but not limited to, increases in blood flow to active brain regions, changes in oxygen level in the blood, increases in metabolic activity (e.g., glucose consumption), changes in electrical potential of neurons, and the release of neurotransmitters. Brain activity can be measured non-invasively by, for example, measuring changes in electrical fields, magnetic fields emanating from the cranium.

As used herein, the term "brain area" refers to a volume of tissue within the human brain, which can be of any shape and which can be characterized anatomically or spatially.

As used herein, the terms "frontal", "anterior", "posterior", "superior" and "inferior" have their customary meanings in anatomy. See, for example, *Stedman's Medical Dictionary*.

Specific locations within the brain, or volumes within the brain, can also be described by reference to three-dimensional coordinate systems. One such system is that described by Talairach and Tournox (*Stereotaxic Coplanar Atlas of the Human Brain* published by Thieme in 1988 ISBN 9783137117018), and is based upon a single brain considered by the authors to be typical. The brain images or maps of individual subjects can be compared to such template brains by visual comparison, or computer software programs can be used which map the individual brains onto a template brain. For example, the Statistical Parametric Mapping (SPM) software, described below, automatically performs spatial registration and normalization of individual brains onto the MNI template. Software is also available which determines the correspondence amongst MNI coordinates and Talairach coordinates (e.g., MRIcro, available at www.cla.sc.edu/psyc/faculty/rorden/mrico.html; see also Rorden and Brett (2000), *Behavioural Neurology*, 12:191-200).

As used herein, the term "voxel" refers to a multidimensional data point corresponding to a specific volume in space, and particularly refers to such a data point obtained from a brain imaging procedure and corresponding to a specific volume within the brain. Voxel size is dependent on the experimental procedure and equipment, notably the resolution of the fMRI instrument. In this application a 1.5

Tesla instrument was used, but instruments up to 7 Tesla are available commercially today.

As used herein, the term "brain activation map" means a set or array of data in which each data point corresponds to a point or volume in a human brain. Each data point can consist of a single datum associated with a brain coordinate, or can consist of a multidimensional data array associated with a brain coordinate. The brain activation map can be displayed as a two- or three-dimensional representation, or can be stored as a data set without being graphically displayed.

As used herein, the term "fragrance sample", is taken to mean:
  any individual material, e.g. a "fragrance ingredient" (which is synonymous with the terms "perfume ingredient" and "perfume material"), which may be an ingredient within an accord or a fully formulated fragrance;
  a mixture of individual materials as defined above, such as for example an accord or a fully formulated fragrance. Mixtures of individual materials may comprise up to 40 fragrance ingredients, for example at least 10, preferably at least 20, more preferably at least 30 fragrance ingredients.

The skilled person will appreciate that a fragrance ingredient may itself comprise many individual chemical compounds and possess a pleasant smell. This distinction is understood by those familiar with the art of fragrance creation. A perfume ingredient or perfume material can be any natural oil or extract, or chemical compound used in a fragrance composition. Natural oils and extracts are described in *The Essential Oils* by E Guenther published by Van Nostrand and may include extracts and distillates from any part of suitable plants: roots, rhizomes, bulbs, corms, stem, bark, heartwood, leaves, flowers, seeds and fruit. Examples of such extracts and distillates include citrus fruit oils such as orange or lemon oil, tree oils such as pine oil or cedarwood oil, herb oils such as peppermint oil, thyme oil, rosemary oil, clove oil or flower extracts such as rose oil, or geranium oil. A wide variety of synthetic odiferous materials are also known for perfumery use, including materials possessing a variety of chemical functional groups, such as acetals, alkenes, alcohols, aldehydes, amides, amines, esters, ethers, imines, nitriles, ketals, ketones, oximes, thiols, thioketones, etc. Without wishing to be limited, in most cases, perfume ingredients are odiferous compounds having molecular weights between 70 mass units and 400 mass units to ensure sufficient volatility. Fragrance ingredients will not contain strongly ionizing functional groups such as sulphonates, sulphates, or quaternary ammonium ions. Perfume ingredients are described more fully in S. Arctander, *Perfume Flavors and Chemicals*. Vols. I and II, Montclair, N.J., the Merck Index, 8th Edition, Merck & Co., Inc, Rahway, N.J. and *Allured's Flavor and Fragrance Materials* 2008 Published by Allured Publishing Corp ISBN 1-932633-42-1 all of which are incorporated herein by reference.

In a first aspect, the present invention provides a method of identifying a fragrance sample which elicits a reward through the dopaminergic pathway wherein the method comprises:
a) submitting a group of subjects to a first protocol comprising:
  having each subject of said group smell a control odour;
  capturing functional Magnetic Resonance Imaging (fMRI) brain scans of each subject smelling the control odour so as to detect the brain activity of each subject;
b) submitting the same group of subjects to a second protocol comprising;
  having each subject of said group smell a fragrance sample to be tested;
  capturing fMRI brain scans of each subject smelling the fragrance sample to be tested so as to detect the brain activity of each subject;
c) averaging the brain activity of all subjects as obtained in the first protocol and in the second protocol; and
d) contrasting the resulting averaged brain activity obtained in the second protocol with the resulting averaged brain activity obtained in the first protocol whereby a number of adjacent activated voxels is determined;
wherein if a cluster of adjacent activated voxels has a volume equal to or greater than a threshold value, or if a cluster has a number of adjacent activated voxels equal to or greater than a threshold value, in at least three brain areas selected from the Midbrain (VTA), Prefrontal Cortex, Striatum and Amygdala-Hippocampus complex, then the tested fragrance sample elicits a reward through the dopaminergic pathway.

Sniffing any odour elicits brain activity due to odour processing, which is detected by fMRI as detailed below. The present invention is based on the surprising finding that simultaneous activation of at least three of the following specific brain areas: the dopaminergic Midbrain (Ventral Tegmental Area), Prefrontal Cortex, Striatum and Amygdala-Hippocampus complex in response to smelling a fragrance sample is evidence that the dopaminergic pathway has been activated.

The method of the invention comprises a first step where subjects within a group of subjects each smell a control odour and the brain activity of each subject is determined using fMRI. The group of subjects typically comprises at least 5 subjects, preferably at least 10 subjects. The control odour is preferably air or an odourless perfumery solvent diluted in air. Any odourless solvent commonly used in perfumery, e.g. di-propylene glycol or triethyl citrate, can be used in the method of the invention. In one embodiment, the control odour can also be a fragrance sample as defined above (e.g. an individual material such as, for example rose absolute, or an accord or an existing fragrance against which a new fragrance is tested) which activates none or only one of the four specific brain areas mentioned above (Midbrain (Ventral Tegmental Area), Prefrontal Cortex, Striatum, Amygdala-Hippocampus complex).

In a second step, the same group of subjects smells a test fragrance sample and the brain activity of each subject is again determined using fMRI.

The control odour and the fragrance sample are delivered to one of the subjects' nostrils via an olfactometer. To avoid the nasal passages becoming dry, the control odour and the sample are preferably humidified before being introduced into the nose.

In a third step, the brain activity of all subjects having smelt the control odour is averaged, and the brain activity of all subjects having smelt the test sample is also averaged.

The next step comprises contrasting the resulting averaged brain activities. This is typically done by subtracting the averaged brain activity of the 'control group' from the averaged brain activity of the 'test group'. As a result of the subtraction the number of adjacent activated voxels in 3D space, i.e. adjacent voxels with significantly different blood flow (or activity), namely voxels which pass student t-test ($p<0.005$) in each brain area studied is determined. The voxel distribution is analysed and clusters of activated voxels are identified. Significant cluster sizes simultaneously in at least three brain areas selected from the Midbrain (Ventral Tegmental Area), Prefrontal Cortex, Striatum and Amygdala-Hippocampus complex indicate that the reward pathway is activated. This procedure is explained in more detail below.

The result of the contrasting step is compared to a threshold value. The threshold value is preferably chosen based upon a comparison of the value of a single voxel to all other values of all other voxels in the brain areas studied. The threshold value can be based either on cluster volume or on the number of adjacent activated voxels in a cluster. Voxels are typically cubes, or cuboids, measuring, for example, about 0.5 mm to about 7 mm per side. In one exemplary embodiment, a voxel of 3.0×3.0×3.75 mm$^3$ is used; in this embodiment the threshold value has been set as being a cluster of a minimum 9 adjacent activated voxels in 3D space, or a cluster (of adjacent activated voxels) volume of at least about 303 mm$^3$.

Alternatively, the subtraction step defined above can be performed by contrasting, for each subject, the brain activity obtained in the second protocol with the brain activity obtained in the first protocol; and then averaging the resulting contrasted brain activity of all subjects.

Brain activity is measured by detecting brain signals; subtracting 'control' signals from 'measured' signals gives signals showing odour stimuli, which are then computed and transformed into a 3-dimensional map as explained below. Brain activity is preferably measured using the blood oxygen level dependant (BOLD) method, which is a recognised technique for measuring brain activity which correlates with the increased energy consumption by the brain and the contrast between oxyhaemoglobin and de-oxyhaemoglobin.

Subject Selection

It is required that subjects be able to read and write and have the capacity to provide informed consent. Potential subjects are excluded if they have current or past psychiatric disorder other than simple phobias but including substance abuse/dependence as determined by the Structured Clinical Interview for DSM-IV Axis I Disorders (SCID-I) (First et al. (1995); a history of neurologic disease; a currently unstable medical condition; used psychotropic medication within 5 half-lives of the procedure time; any metal implants or shrapnel which would make an MRI procedure unsafe; irremovable medical devices such as pacemakers or fixed hearing aids; previous inability to tolerate an MRI procedure; or claustrophobia severe enough to induce substantial anxiety in closed spaces. Other exclusion criteria include age under 9 years, history of any disease known to have an impact on the olfactory function (e.g. Diabetes, Parkinson Disease, Renal failure, etc). A complete ENT (ear, nose and throat) examination excluded pathology that could interfere with the olfactory ability: acute or severe chronic rhinitis or sinusitis, severe septum deviation, history of trauma, nasal polyps, etc. Subjects also completed a handedness inventory for the participation in the experiment. It is preferred to avoid variations due to gender or handedness, so subjects are selected to comprise panels or groups of a single sex and having the same predominant hand.

Having passed the selection criteria above only normosmic subjects were selected for the test. Various tests are available commercially to ensure that subjects have a normal sense of smell. Such tests vary from odor identification tests to more sophisticated threshold and discrimination tests. Any suitable test should be validated and reliable. In the example given below a "Sniffin' Sticks" test was used to assess the olfactory function. For further information on Sniffin Sticks see T Hummel, B Sekinger, S R Wolf, E pauli, and G Kobal Sniffin Sticks: *Olfactory Performance Assessed by the Combined Testing of Odor Identification, Odor Discrimination and Olfactory Threshold* in Chem. Senses 1997 vol 22 pp 39-52 or T Hummel, K Rosenheim, C-G Konnerth and G Kobal *Screening Olfactory Function with a Four Minute Odor Investigation Test Reliability Normative Data and Investigations in Patients with Olfactory Loss* in Ann. Otol. Rhinol. and Laryngol. 2001 vol 110 pp 976-981. Sniffin Sticks are available from Burghardt Gmbh Wedel Germany. For odour presentation the cap is removed by the experimenter for approximately 3 s and the pen's tip is placed approximately 2 cm in front of both nostrils. The odour identification test involves the assessment of 12 common odours (cinnamon, banana, lemon, liquorice, pineapple, coffee, cloves, rose, leather, fish, orange, peppermint). Using a multiple choice task, identification of individual odourants was performed from a list of 4 descriptors per odour. The interval between odour presentations was 20-30 s. All measurements were performed in a quiet, air-conditioned room. 10 or more correct responses were required for participation in the subsequent experiments.

Preparation of Test Samples

Test samples of fragrance materials were prepared to have equal olfactive intensity using the static method of ASTM E544 (1999) Standard Practice for Referencing the Intensity of Ambient Odours Procedure B Static Methods using n-Butanol as a reference.

fMRI Scanner

Any suitable MRI device can be used to achieve the desired fMRI images, which is capable of operating using a spin echo, echo planar imaging (SE-EPI) sequence. This EPI protocol is optimized detecting subtle changes in blood oxygen levels in the brain over time. EPI scanning is an effective way to measure changes in the blood oxygen level dependent (BOLD) signal which has been shown to correlate reliably with changes in neural activity. Scans were taken which covered the whole brain allowing the continuous monitoring of the whole brain throughout each assessment. Suitable MRI scanners are available from Siemens AG, Phillips, GE Healthcare, Varian, Toshiba and Hitachi.

Olfactometer

Any olfactometer can be used, which is suitable for use with an fMRI scanner. Suitable olfactometer designs have been reported by Koba/(*Electroencephalography and clinical neurophysiology* 71, 241-250, 1988) and Sobel (*J. Neuroscience methods* 78, 115-123, 1997) and suitable commercial olfactometers are available from Burghart Medezintechnik GmbH of Wedel Germany. To minimize head movement odorants are applied intranasally by means of a canula with an inner diameter of 2-3 mm. This canula is inserted for −1 cm into the naris such that its opening lies beyond the nasal valve. Presentation of odourants does not simultaneously activate mechano- or thermoreceptors in the nasal mucosa, as odour pulses are embedded in a constantly flowing thermostatted (36° C.), humidified (80% RH) air stream (typically 6-8 l/min) which quickly becomes undetectable after a few minutes. Hence, subjects do not perceive any change when the olfactometer switches from a no-stimulus to a stimulus condition and vice versa, nor do subjects experience any interference from mechanical or thermal stimulation. Air flow rates are determined by mass-flow controllers, which along with switching valves, are computer-controlled. Thus the equipment allows the setup of sequences of stimuli with different quality, intensity, duration, or interstimulus interval and multiple repetitions to achieve the maximum accuracy and precision in sample presentation.

Statistical Data Analysis

Methods for the statistical analysis of changes in brain activity are well known in the art and, for some brain activity measuring devices, computer software packages are commercially available which are specifically adapted to analyze the data. For example, SPECT, PET or MRI data can be analyzed using the Dot or EMMA (Extensible MATLAB Medical image Analysis) packages which are both freely available from the MNI, or the SPM software package which is freely available from the Functional Imaging Laboratory of the Wellcome Department of Imaging Neuroscience at the University College of London, UK (www.fil.ion.ucl.ac.uk/spm/). The EMMA and SPM software are based upon the MATLAB® programming language (MathWorks, Inc., Natick, Mass.), with additional routines in the C programming language. An SPM module is incorporated into the commercially available MEDx software (Medical Numerics, Inc., Sterling, Va.). The SPM software uses a parametric statistical model at each voxel, using a general linear model to describe the variability of the data in terms of experimental and confounding effects, and residual variability. Hypotheses expressed in terms of the model parameters are assessed at each voxel with univariate statistics. Temporal convolution of the general linear model for fMRI enables the application of results from serially correlated regression, permitting the construction of statistic images from fMRI time series. The multiple comparisons problem of simultaneously assessing all the voxel statistics is addressed using the theory of continuous random fields, assuming the statistic image to be a good lattice representation of an underlying continuous stationary random field. Results for the Euler characteristic lead to corrected p-values for each voxel hypothesis. In addition, the theory permits the computation of corrected p-values for clusters of k voxels exceeding a given threshold, and for entire sets of supra-threshold clusters, leading to more powerful statistical tests at the expense of some localizing power (see Friston et al., *Magnetic Resonance in Medicine* 35 346-355 1996 and citations thereof).

The statistical approach used to evaluate the general set of fMRI data is a time-series variant of the Analysis of Variance (ANOVA) form of a general linear model. The statistical analysis tests each voxel of the brain, for each subject, against the null hypothesis (that over the duration of the testing the rise and fall of the BOLD signal coming from that voxel does not correlate with the onsets and offsets of the cycles of presentation of odours). A weighted model is created that begins with a simple square wave type model of the on-off timing events for a single task variable of interest. The ANOVA model allows regressors to be used to model nuisance variables. In the present invention, the global signal strength of the whole brain is used as such a regressor. The global signal strength of the brain will account for fluctuations in the brain caused by respiratory cycles, cardiac flow cycles, blinking etc. These signal variations occur across the whole brain, and may often be a greater magnitude than the localized changes in the BOLD signal resulting from the olfactory signal. These signal variations occurring across the brain can be subtracted from the measured fMRI signals to show the signals resulting from the odour stimuli.

The resulting product of the ANOVA computation on a single-person's fMRI data is a 3-dimensional matrix of t-values which can be represented as a 3 dimensional map.

This t-value map can then be converted into a probability map (a map of corresponding p-values) and the results can be displayed graphically at whatever threshold is desired (e.g. $p<0.05$). The results may be overlain on a higher-resolution MRI image, in order to facilitate identification of finer-grained cortical structures.

In order to combine the data from more than one subject, each subject's brain is first normalized into a common 3-dimensional stereotactic space before each individual's t-map is computed. Then the value of the sum of the contrast weights for each voxel from each subject computed during the ANOVA (basically, the numerator of the t-statistic) is entered as a single data point in a new, "second-level" t-statistic computation. In this second-level computation, then, the mean value for each voxel across subjects is modeled as the effect term and the variance between subjects as the error term. An important consequence of this approach to keep in mind is that it is very unlikely that a voxel will show significant activation on the group-level map, unless virtually all of the subjects show activation at that voxel. Also brain areas are only considered to be activated if a number of adjoining voxels show a statistical significance above the designated probability standard.

For purposes of statistical analysis and graphical display, the raw data on brain activity is usually grouped into voxels corresponding to fixed volumes of the subject brain. The voxel size can be varied depending upon the resolution capability of the brain activity measuring device or the desired degree of precision in identifying brain regions. It should be noted, however, that smaller voxels have worse signal to noise ratios and greater susceptibility artifacts due to partial volume effects. Typically, voxels are cubes, or cuboids measuring, for example, 0.5 mm to 7 mm per side (e.g., $3.0 \times 3.0 \times 3.0$ mm$^3$). The data can then be displayed graphically by colour-coding the voxels according to some statistical value and showing cross-sections in which levels of activity or changes in levels of activity are mapped in two-dimensions. By generating a series of such co-planar cross-sections, the entire brain volume can be mapped.

When conducting statistical analyses on brain images, investigators can select an appropriate probability value for assessing statistical significance. The particular value chosen can vary depending upon the purpose of the statistical analysis and the level of certainty required. In the studies described in the example the level for statistical significance was chosen to be $p<0.005$.

The method described above makes it possible to identify fragrance samples which elicit a reward through the dopaminergic pathway.

Accordingly, in another aspect the present invention relates to fragrance samples identified by said method.

Such fragrance samples may be accords or fully formulated fragrances, or may be used to formulate accords or fully formulated fragrances that will in turn elicit a reward through the dopaminergic pathway when smelled or worn.

A further aspect of the invention thus relates to a method for preparing an accord or a fully formulated fragrance which comprises:
a) screening at least one fragrance sample for its (their) ability to elicit a reward through the dopaminergic pathway;
b) if the sample(s) is (are) identified to elicit a reward through the dopaminergic pathway, formulating said fragrance sample(s) into an accord or a fully formulated fragrance.

In one embodiment, the accord or the fully formulated fragrance comprises vanillin.

Fragrance samples identified to elicit a reward through the dopaminergic pathway can also be used in consumer products such as household products, laundry products, personal care products and cosmetic products (including alcoholic fragrances and eau de cologne). Such products include detergents, e.g. laundry detergents, fabric softeners and conditioners, shampoos, hair conditioners, skin lotions, body oils, deodorants, sunscreen products.

The invention is illustrated by the following, non-limiting examples.

Example 1

18 female right handed subjects were selected to take part in the fMRI experiment. The following pleasant odours were smelt according to the procedure detailed below:

Vanillin, prepared by recrystallization of a commercial quality, was used as a 15% solution in di-propylene glycol;

Thesaron® (the trade name of Ethyl trans-2,2,6-trimethylcyclohexanecarboxylate) is available from Takasago, and was used as a 20% solution in di-propylene glycol;

Rose absolute from Morocco (available from Biolandes, France) was used as a 0.5% solution in di-propylene glycol;

Isobornyl acetate (IBA, available from Arco, France) was used as a 1% solution in di-propylene glycol.

The samples were prepared to have equal odour intensity. Odour stimuli were delivered to the right nostril of subjects in the scanner via an air dilution computer controlled olfactometer (Burghart OM8b), that allowed alternation between olfactory (ON) and non olfactory (OFF) stimulation conditions in a 20 s ON/20 s OFF block design. Stimuli were delivered for 1 s every 2 s during the ON period. Every ON period was followed by a matching 2 s baseline OFF period when only humidified pure air (as control odour) was delivered. Each of the stimuli was presented in alternating blocks in a 240 s resulting scanning run. Four protocols with randomized block order were constructed and applied in randomized order across subjects. After the functional runs, anatomy scans were acquired. Between runs 2 min breaks were included. The overall scanning time was approximately 50 min. At the end of the scanning session, subjects were offered the 4 stimuli again in the same block set-up in a randomized order and asked to rate them for intensity, hedonics and arousal.

Data was acquired using a 1.5 T MR-scanner (Sonata; Siemens, Erlangen, Germany). For anatomic overlays a T1-weighted (turboflash sequence) axial scan with 224 slices, voxel size of $1.6 \times 1.1 \times 1.5$ mm$^3$, a repetition time (TR) of 2130 ms, echo time (TE) of 3.93 ms, and two averages (2130/3.93/2) was acquired. fMRI studies were performed in the axial plane (oriented parallel to the planum sphenoidale to minimize bone artifacts) using a multi-slice spin-echo echo-planar imaging (SE-EPI) sequence. Scan parameters included a 64×64 matrix, voxel size of $3 \times 3 \times 3.75$ mm$^3$, TR of 2500 ms, and a TE of 35 ms. A total of 120 images were acquired at each of 24 slice locations per paradigm.

Neuro-imaging data were pre- and post-processed using SPM5 (Wellcome Department of Cognitive Neurology, London, UK, implemented in Matlab R2007b; The MathWorks, Inc., Natick, Mass., USA). Functional data were registered, realigned to correct the problems of movement and then coregistered to the corresponding structural images. Further the spatially normalized (stereotactically transformed into MNI ICBM152-space; MNI-template supplied by SPM2) and smoothed images (by means of a $7 \times 7 \times 7$ mm$^3$ FWHM Gaussian filter) were analyzed.

Data analysis for the samples is summarized in table 1. A cluster of a minimum 9 adjacent activated voxels in 3D space was set as the threshold value ($p<0.005$), for the experiment based on the SPM analysis. "YES" means at least 9 adjacent voxels were activated. The contrast was performed versus no odour (air).

TABLE 1

| | Vanillin | Thesaron | Rose Absolute | IBA |
|---|---|---|---|---|
| Midbrain (VTA) | YES | NO | NO | NO |
| Prefrontal cortex | YES | YES | YES | YES |
| Striatum | YES | YES | NO | YES |
| Amygdala-Hippocampus complex | YES | NO | NO | NO |

In conclusion, of the materials tested, vanillin showed activation in all brain areas belonging to the dopaminergic pathway. The other pleasant odours did not activate the dopaminergic pathway.

Example 2

The procedure of example 1 was repeated contrasting vanillin with rose absolute as the control odour (both odours being prepared as in example 1). A cluster of a minimum 9 adjacent activated voxels in 3D space was set as the threshold value ($p<0.005$), for the experiment based on the SPM analysis. "YES" means at least 9 adjacent voxels were activated. The results are presented in Table 2.

TABLE 2

| | Vanillin |
|---|---|
| Midbrain (VTA) | YES |
| Prefrontal cortex | YES |
| Striatum | NO |
| Amygdala-Hippocampus complex | YES |

In this example, vanillin also showed activation of the dopaminergic pathway.

Example 3

A further experiment was conducted using a similar experimental procedure as for Example 1, the changes being as follows.

The olfactometer used was based on the guidance of odourless air through glass vessels filled with liquid fragrance samples, such that odour saturated air in the headspace of the vessel above the liquid fragrance sample is swept towards the subject. Humidified odour stimuli were either presented in a pulsatile manner to the subjects or wasted into the environment. During times when subjects were not presented with odour stimuli they received odourless, humidified air (as control odour). Typically, the pulse length was 1 s, the interval was 2 s. The typically used airflow was 2 l/min; the odours (test and control) were presented to both nostrils, so that 1 l/min was presented to each nostril. This pulsatile stimulation with odour typically went on for 21 s (so called ON phase), then the system switched to odourless air, which was presented for the next period of 21 s (so called OFF phase). Stimulus duration, interstimulus interval, duration of ON and OFF phases were computer controlled, so that the sequences always followed the course that had been programmed before onset of the session. The scanning procedure was then as in example 1.

In the above protocol, 26 women smelt Vanillin (as a solution in di-propylene glycol –3 g Vanillin in 10 g solvent) and an accord, designated under Takasago's reference DGFRUI067K, with a red fruit character which does not contain any Vanillin (said accord was used undiluted). As described above, the odours were contrasted against air. A cluster of a minimum 9 adjacent activated voxels in 3D space was set as the threshold value (p<0.005), for the experiment based on the SPM analysis. "YES" means at least 9 adjacent voxels were activated. The results are presented in Table 3.

TABLE 3

|  | Vanillin | DGFRUI067K |
|---|---|---|
| Midbrain (VTA) | NO | NO |
| Prefrontal cortex | YES | YES |
| Striatum | YES | YES |
| Amygdala-Hippocampus complex | YES | YES |

In this example, vanillin again showed activation of the dopaminergic pathway. The tested accord containing no vanillin also showed activation of the dopaminergic pathway.

The invention claimed is:

1. A method of identifying a fragrance sample that elicits a brain activity through a dopaminergic pathway, wherein the method comprises:
   a) a first protocol comprising:
      having each subject of a group of subjects smell a control odour;
      capturing functional Magnetic Resonance Imaging (fMRI) brain scans of each subject smelling the control odour so as to detect a brain activity of each subject;
   b) a second protocol comprising:
      having each subject of said group smell a fragrance sample to be tested;
      capturing fMRI brain scans of each subject smelling the fragrance sample to be tested so as to detect a brain activity of each subject;
   c) averaging the detected brain activity of all subjects of said group in the first protocol and averaging the detected brain activity of all subjects of said group in the second protocol; and
   d) contrasting the resulting averaged brain activity obtained in the second protocol with the resulting averaged brain activity obtained in the first protocol whereby a number of adjacent activated voxels is determined; and
   e) identifying the fragrance sample which elicits brain activity through the dopaminergic pathway where a cluster of adjacent activated voxels having a volume equal to or greater than a threshold value, or where a cluster having a number of adjacent activated voxels equal to or greater than a threshold value, is simultaneously activated in at least three of the following brain areas: Ventral Tegmental Area (VTA), Prefrontal Cortex, Striatum and Amygdala-Hippocampus complex,
   wherein the volume or number of activated voxels for identifying the fragrance sample is identified by statistical parametric mapping (SMP) analysis of the captured fMRI brain scans.

2. The method according to claim 1, wherein the control odour is air or an odourless perfumery solvent diluted in air.

3. The method according to claim 1, wherein the group of subjects comprises at least 5 subjects.

4. The method according to claim 1, wherein the group of subjects comprises at least 10 subjects.

5. The method according to claim 1, wherein the threshold value of the volume that the cluster of adjacent activated voxels has is 303 mm$^3$.

6. The method according to claim 1, wherein the threshold value of the number of adjacent activated voxels is nine.

7. A method according to claim 1, wherein the fragrance sample identified to elicit brain activity through the dopaminergic pathway is formulated for a product,
   wherein the product is selected from the group consisting of a household product, a laundry product, a personal care product and a cosmetic product.

8. The method according to claim 7, wherein the product is the household product.

9. The method according to claim 7, wherein the product is the laundry product.

10. The method according to claim 7, wherein the product is the cosmetic product.

11. A method for preparing an accord or a fully formulated fragrance which comprises:
    a) screening at least one fragrance sample for its (their) ability to elicit brain activity through the dopaminergic pathway;
    b) if the fragrance sample(s) is (are) identified to elicit brain activity through the dopaminergic pathway, formulating said fragrance sample(s) into an accord or a fully formulated fragrance;
    wherein step a) is carried out by the method defined in claim 1.

12. The method according to claim 11, wherein the accord or the fully formulated fragrance comprises vanillin.

* * * * *